US006669682B1

(12) United States Patent
Gibson et al.

(10) Patent No.: US 6,669,682 B1
(45) Date of Patent: Dec. 30, 2003

(54) VETERINARY DELIVERY DEVICE AND METHOD

(75) Inventors: David John Michael Gibson, Wellington (NZ); Christopher Seton Norris, Palmerston North (NZ)

(73) Assignee: Bryher Holdings Limited, Wellington (NZ)

(*) Notice: Subject to any disclaimer, the term of this patent is extended or adjusted under 35 U.S.C. 154(b) by 0 days.

(21) Appl. No.: 09/622,059

(22) PCT Filed: Feb. 25, 1999

(86) PCT No.: PCT/NZ99/00022

§ 371 (c)(1), (2), (4) Date: Aug. 25, 2000

(87) PCT Pub. No.: WO99/43269

PCT Pub. Date: Sep. 2, 1999

(51) Int. Cl.[7] ........................ A61K 9/22; A61M 37/00; G08B 23/00

(52) U.S. Cl. .................... 604/890.1; 604/131; 604/179; 340/573.3; 340/539.12

(58) Field of Search .......................... 119/712; 604/183, 604/890.1, 891.1, 131, 151, 146, 500, 65, 174, 179, 67, 141, 89.1; 424/438; 206/457; 600/463, 104, 588

(56) References Cited

U.S. PATENT DOCUMENTS

| | | | | |
|---|---|---|---|---|
| 4,040,422 A | | 8/1977 | Kuhn | 128/223 |
| 4,707,685 A | * | 11/1987 | Carrier et al. | 340/539 |
| 4,714,462 A | * | 12/1987 | DiDomenico | 604/67 |
| 5,511,560 A | * | 4/1996 | Begouen | 600/551 |
| 5,658,133 A | * | 8/1997 | Anderson et al. | 417/479 |
| 5,728,070 A | * | 3/1998 | Walker et al. | 604/179 |
| 5,980,496 A | * | 11/1999 | Jacobsen et al. | 119/606 |
| 6,158,676 A | * | 12/2000 | Hughes | 239/337 |
| 6,193,704 B1 | * | 2/2001 | Winters | 604/131 |
| 6,203,528 B1 | * | 3/2001 | Deckert et al. | 604/131 |
| 6,375,649 B1 | * | 4/2002 | Jellie | 604/131 |

FOREIGN PATENT DOCUMENTS

| | | |
|---|---|---|
| FR | 2450103 | 9/1980 |
| NL | 198187 | 8/1985 |
| NZ | 111985 | 8/1957 |
| NZ | 261795 | 6/1997 |
| WO | WO93/02634 | 2/1993 |
| WO | WO94/17753 | 8/1994 |
| WO | WO96/29025 | 9/1996 |
| WO | WO99/18884 | 4/1999 |

OTHER PUBLICATIONS

Patent Abstracts of Japan No. 97–206965/19 and JP 09056735 A (MIYAZAWA), Mar. 4, 1997.

* cited by examiner

*Primary Examiner*—Michael J. Hayes
*Assistant Examiner*—Roz Ghafoorian
(74) *Attorney, Agent, or Firm*—Jacobson Holman PLLC

(57) ABSTRACT

An apparatus for transporting fluid between a reservoir and a natural body cavity. The direction of flow can be in either direction. In a preferred embodiment the reservoir is fitted with a pump to advance fluid from the reservoir into the cavity. A locator forming a part of the apparatus is adapted so at least part of it is fitted through a natural orifice and retained within the natural body cavity. The apparatus includes a securing device which holds it in place on an animal during the normal cavities of that animal.

35 Claims, 9 Drawing Sheets

VETERINARY DELIVERY DEVICE AND METHOD

TECHNICAL FIELD

The invention relates to a method and an apparatus for the transport of one or more fluid substances between respective reservoirs and predetermined sites in or on the body of an animal.

In particular, the invention enables one or more substances to be delivered to, and/or collected from, respective sites in or on the body of an animal. Such sites include internal sites, such as natural body cavities, e.g. vaginal, nasal and buccal cavities.

The method and apparatus is particularly suitable for unsupervised substance transport over an extended period on ambulatory animals.

The invention is suited to use on an animal and particularly to domestic cattle or other quadrupeds such as pigs, goats, sheep or deer. The invention could be adapted for use with birds. In a particular embodiment, it relates to an apparatus attached to a cow for the delivery of a substance such as a therapeutic agent, to the cow.

BACKGROUND ART

Substance delivery devices are known for administration of substances to the human body.

U.S. Pat. No. 3,547,322 discloses an apparatus for intravenous administration, to a human patient, of a fluid from a container supported by a harness and secured externally to the body of the patient. The apparatus is said to allow the patient to move about, or be moved about, during such intravenous administion. The apparatus is unwieldy and totally unsuited for unsupervised field use on freely ambulatory animals.

U.S. Pat. No. 5,728,070 discloses a portable medication dispenser system in which a harness, e.g. a waist belt and an optional shoulder strap, externally worn by a human patient supports a container holding the medication, e.g. in a pocket at one location, and a pump at another location. Tubing interconnects the container, the pump and a catheter by which medication is introduced into the body of the patient. The harness is formed from elasticized fabric. The system is not suited to the delivery and collection of substances on freely ambulatory field animals left unsupervised for an extended period.

The delivery of substances to living non-human animals has commonly involved injections or devices requiring surgical implantation or retention within a natural body cavity, for example, the rumen or the vagina. The administration of substances by injection often causes abscesses and high levels of the substances are frequently found at the injection site at slaughter. Injections also can damage the hide and are therefore restricted to particular sites, e.g. to the neck region. Many drugs do not achieve their maximum therapeutic action through conventional injection techniques. The therapeutic action of such drugs is improved considerably when delivered at a controlled rate to maintain optimum drug concentration for a specific period. In a typical drug injection, a greater drug concentration than necessary must be administered to keep the drug concentration within the effective therapeutic margin for the minimum period necessary for treatment. With controlled drug infusion, the drug can be given at a precise rate that will keep the drug serum concentration above a therapeutic minimum and below toxic levels. Many drugs reach their fill potential effectiveness only through precise delivery over extended periods of time.

In animal husbandry the administration of drugs to animals involves a great deal of handling which is laborious for the handler and stressful for the animals. Often animals must be brought in from long distances making prolonged or frequent treatment difficult if not prohibitive. In some cases the stress levels caused by handling stock can impair the performance of the treatment, this is particularly true in deer. Many drugs are given in slow release capsules that can cause problems when still remaining in the animal at slaughter.

Many formulations are designed for long release to reduce stock handling requirements but concentrations often fall below the effective therapeutic levels long before the next dose is administered thus increasing the risk of drug resistance. Bacterial drug resistance is a growing problem that affects both animals and humans and commonly arises from the ineffective administration of drug treatments. Parasite drug resistance is now a major problem particularly with anti-parasite drugs such as anthelminthics.

Devices for implantation or insertion require a means for releasing the substance into the body. This may be by controlled diffusion or by the action of a pump. Some devices incorporating pumps use a battery as a power source linked to the pump via simple electronic circuitry. Difficulties arise when internally located devices, such as surgically implanted or intra-ruminal devices, remain in animals at slaughter.

One application of such devices has been the control of the timing of oestrus of domestic animals.

U.S. Pat. No. 3,499,445 discloses the blocking of oestrus by the surgical implantation of a pellet containing a hormonal medicament, and the subsequent initiation of oestrus by the subsequent surgical removal of the pellet.

There are many disadvantages in techniques requiring surgical implantation of substance delivery devices. The device requires surgical intervention for implantation and for removal of the device. There is limited control over dose timing and dose rate. There is no interruption of the dose or variation of the dose substance without surgical intervention. There is no indication of satisfactory operation of the device and no monitoring of physiological or other animal parameters. Substances cannot be collected from the animal. There is a wide variation in the uncontrolled rate of delivery of the substance, and the volume of material that can be delivered is limited by the size of the surgical implant.

Many drug treatments on firs require the sequential and accurately timed delivery of more than one substance to achieve the desired result. This is particularly true of hard to breed stock that require treatment with up to three hormones in a precisely timed delivery programme to effect oestrus. These types of treatment require frequent visits by the veterinarian and are therefore normally reserved for valuable stock.

Some cattle problems such as facial eczema are treated with daily drenches of minerals in low amounts. This is difficult enough with dairy or milking stock but is a particular problem for dry stock, which must be yarded each day.

WO 96/00106 discloses an implantable drug delivery pump system including a sensor, a pump controller, pumps and delivery systems, all preferably implanted within a body. The pumps deliver a controlled volume or a controlled rate of two or more substances, e.g. an agent and counter-agent, to the body, in response to a body condition sensed by the sensor, e.g. temperature, pressure or the presence of glucose or other constituents. The pumps are preferably electrically controlled and may be any conventionally known pump, e.g. piston, peristaltic or centrifugal.

WO 94/01165 discloses a medication-administering device in the form of a 'smart' capsule for introduction into a body cavity. The capsule is said to be particularly suited to being taken orally, but may form a suppository for taking other than orally, or may be surgically introduced to a body. The capsule casing is insoluble in body cavity fluids and contains a reservoir containing the medication which is expelled into the body cavity by a pump driven by an electrolytically-generated gas. A microprocessor controls the rate of delivery of the medication which may be varied in response to body conditions, eg pH, temperature, sound or moisture, monitored by sensors included in the capsule. An electrolytic cell co-operates with body fluids surrounding the capsule to generate electrical power to supply the micro-processor and the gas generator. The capsule may also include a radio transceiver enabling the location of the capsule to be monitored, or the operation of the capsule to be controlled, from outside the body.

The insertion of a device completely within a body cavity imposes several limitations and difficulties. The size of a device is limited by the size of the body cavity of the animal within which it is to be inserted. The dimensions of any retaining means are also limited by the size of the body cavity. The size of any batteries required, and therefore the length of time over which the device may be expected to operate, is also limited The quantity of substance that can be delivered or collected is also limited by the dimensions of the cavity into which the device is to be inserted.

Other problems of inserted devices relate to materials which are incompatible or at least undesirable for use within an animal body: e.g. lithium batteries.

Such substance delivery devices also require a means for retaining the device within the cavity of the animal. Without a reliable retention means, the device may be expelled by the animal or may simply fall out.

A device inserted into body cavities may be subject to natural muscular actions, e.g. peristalsis, tending to expel the device. This can cause problems with retention of devices. It is therefore desirable that systems provide confirmation that they remain inserted and correctly located Known methods of retaining devices in body cavities include com-pressible helical coils, flexible lobes or arms which can splay outwardly from the device once the device is inserted within the body cavity, and distensible ribs which can be distended by plunger action once the device has been inserted. When extended, the projections engage the cavity walls to assist in retention of the device.

WO 96/29025 discloses an apparatus for retaining a substance delivery device in a body cavity, eg intravaginal and intranirninal devices for domestic animals such as cows. The apparatus has multiple flexible arms which splay out-wardly after insertion into a body cavity to retain the apparatus therein. The arms are said to bend without break-ing in response to peristaltic waves within the cavity and to return to their fully extended position once peristaltic waves have passed. The delivery device is said in one embodiment to include a battery which powers piezo pumps, preferably three, for delivering substances contained in reservoirs, under control of a microprocessor. A possible application, in which the apparatus dispenses different doses of different hormones over predetermined times to positively define the date of oestrus, is disclosed. Also disclosed is the possibility that the microprocessor makes a determination of one or more physiological parameters monitored by one or more sensors, e.g. temperature, acidity viscosity and odor, before controlling the timing or the amount of a delivery of a substance to the body.

The volume of material that can be delivered by this device is limited by the volume that can be accommodated in the body cavity. NZ 207341 is a further example disclosin, a device not requiring surgical insertion into a body cavity of an animal and which produces a controlled rate of release into the body, of leachable chemicals incorporated into the device. NZ 207341 discloses a device having a spine with two resiliently hinged legs biased into a splayed disposition in which the device is T-shaped. With the legs folded together, the device may be inserted into the body cavity. A coating on the spine incorporates a chemical which leaches out when exposed to body fluids.

The device of NZ 207341 does not provide for control of the timing or rate of substance delivery or of the substance delivered. It provides no indication of satisfactory operation of the device. It does not monitor physiological or other parameters. It cannot collect substances. There is a wide and uncontrolled variation in the rate of delivery of a substance, and the volume of material to be delivered is limited by the volume that can be incorporated into the coating on the device which it self must be accommodated within a body cavity.

In devices employing outwardly-extending finger-like projections to engage the walls of a body cavity, the pro-jections can interfere with the flow of normal body secre-tions. Where a device is implanted in a vaginal cavity, the projections can impair the flow of vaginal mucous. The fingers operate by pressing outwardly on the vaginal walls, holding them apart. This impairs the normal peristaltic action, retarding the normal mucous flow, and provides a void which allows an undesirable build-up of mucous around the device. The build-up of mucous often becomes infected and can interfere with the release of therapeutic material from the device and its uptake by the body.

In WO93/02634 there is described a device for artificial insemination of sows. The device is made up of a frame consisting of two hoops and a spinal column fitted over the back of a sow with a holder for a sperm tube. There is a small extension of the sperm tube extending into the vagina. The extension does not have a locator which is retained in a predetermined position within the vagina and it is possible that in the process of insemination seminal fluid in the sperm tube may well be lost or not delivered within the vagina.

Intravaginal devices often do not provide an outwardly available indication providing confirmation of the continu-ing presence of tie device in situ, or of its correct operation.

It is an object of this invention to go some way towards overcoming these disadvantages or at least to offer the public a useful choice.

SUMMARY OF THE INVENTION

Accordingly, the invention may be said broadly to consist in an apparatus for transporting a fluid through a natural orifice of an animal between a reservoir and a natural body cavity of said animal which comprises:

a reservoir for such fluid, a locator at least a part of which is adapted to pass through a natural orifice and be fitted and retained within a predetermined position within said body cavity, a conduit communicating between said reservoir and said part of said locator, means for advancing said fluid through said conduit between said reservoir and said body cavity, and means to secure said apparatus to said animal.

Preferably said reservoir has two or more compartments and said conduit consists of either two passages or means to deliver alternatively different fluids therethrough.

Preferably said reservoir comprises a replaceable cartridge or cartridges.

Preferably said part of said locator includes an orifice and a portion of said conduit is integral with said locator and communicates with said locator orifice.

Preferably said part of said locator is adapted to be fitted in said cavity by the provision thereon of penetration controlling means.

Preferably said penetration controlling means is adapted to engage body surfaces of said animal.

Preferably said penetration controlling means is adapted to restrain over-penetration of said part of said locator beyond said predetermined position in said cavity.

Preferably said part of said locator is adapted to be retained in said body cavity by the provision thereon of external retaining means.

Preferably said external retaining means is integral with said penetration controlling means.

Preferably said part of said locator which is adapted to pass through a natural orifice of said body cavity and be fitted for retention at a predetermined position within said body cavity is elongate and without any lateral arms or lateral extensions.

Preferably said locator is made of stiff but flexible material.

In one alternative said means for advancing said fluid is gravity.

In another embodiment said means for advancing said fluid is a pump.

Preferably said pump is provided with metering means.

Preferably said apparatus includes a microprocessor for controlling the operation of said pump.

Preferably said apparatus includes detecting means associated with said microprocessor.

Preferably said detecting means are associated with said locator.

Preferably said microprocessor is programmable to control said pump to transfer a predetermined amount of fluid at a time and in a volume determined by signals from said detecting means.

Preferably said reservoir, pump and microprocessor are located in the same housing.

Preferably said locator shaft is curved to conform to the shape of said cavity.

Preferably said microprocessor is programmable to deliver a predetermined amount of fluid at a time and in a volume determined by signals from said sensor.

Preferably said apparatus is adapted to deliver said fluid from said reservoir to a particular site in said cavity.

In an alternative embodiment said apparatus is adapted to deliver said fluid from said body cavity to said reservoir.

Preferably said means to secure said apparatus to a said animal where said animal orifice is rearward facing and said animal is a quadruped includes a first strap adapted to extend in use transversely around the body of said animal and a second strap adapted to extend in use longitudinally rearwardly therefrom along the back of said animal and encircle the proximal end of its tail.

Preferably there is provided a pouch on said second strap for receiving said reservoir and said advancing means.

Preferably there is provided a broadened flexible but stiff portion in said first strap adapted to assist in use in retaining said apparatus on said animal.

In one embodiment said external retaining means is attached to said second strap.

Alternatively said external retaining means is secured with an adhesive to the body of said animal.

In another embodiment said apparatus is adapted to be fitted to the head of an animal, said locator being adapted to be fitted and retained in its mouth.

In another embodiment said apparatus is adapted to be fitted to the head of an animal, said locator being adapted to be fitted and retained in its nasal passage.

In one embodiment of head mounted apparatus said reservoir is mounted in a position above the end of said conduit remote from said reservoir.

In another embodiment the invention may be said broadly to consist in a method for transporting a fluid between a reservoir and a natural orifice into a natural body cavity of an animal which comprises the steps of securing an apparatus as defined herein immediately above with a par of said locator inserted through a natural orifice of said body cavity into said body cavity and operating said apparatus to transfer said fluid between said reservoir and a predetermined site in said body cavity.

Preferably said animal is a quadruped

Preferably said cavity is a vaginal cavity.

Preferably said cavity is a buccal cavity.

Preferably said cavity is a nasal cavity.

Preferably said part of said locator is retained at said predetermined position within said body cavity by engagement of said retaining means with body surfaces of said animal.

Preferably said apparatus is operated to deliver fluid from said reservoir to said body cavity.

Preferably said apparatus is operated to deliver fluid from said body cavity to said reservoir.

In another embodiment the invention consists in a method of controlling the onset of oestrus of a female animal which comprises the steps of securing to said animal an apparatus as defined above with said part of said locator inserted into a natural body cavity of said animal and operating said apparatus to deliver an oestrus-controlling hormonal fluid from said reservoir to said body cavity.

Preferably said apparatus includes detecting means and indicating means, including the steps of operating said detecting means to detect an oestrus-related parameter and operating said indicating means to provide an indication of an oestrus-related state in response to said detected oestrus-related parameter.

In another embodiment the invention consists in a locator comprising a shaft portion adapted to be inserted through a natural orifice into a natural cavity of an animal to sit in a predetermined position, said shaft portion being to self locate in said natural cavity at said predetermined position and external retaining means adapted to maintain said shaft portion at said predetermined position in said cavity.

Preferably said shaft portion is shaped to conform to the interior shape of said body cavity without distorting said cavity.

Preferably said retaining means is attachable to said animal.

Preferably said shaft portion is adapted to self locate by the provision of penetration control means at a proximal end of said shaft, said penetration control means in use engaging an outer surface of said animal at or adjacent said animal orifice.

Preferably said penetration control means includes a lateral extension at a proximal end of said shaft portion.

In another embodiment said lateral extension extends substantially in a single direction transverse to said shaft portion.

In a further embodiment said lateral extension extends substantially in two mutually opposite directions transverse to said shaft portion.

Preferably there is included a sensor associated with said locator to sense a condition in said animal.

Preferably there is included an integral reservoir and fluid advancing means associated therewith.

The invention also consists in a method for providing a veterinary service through a natural body orifice of a natural cavity of an animal which comprises inserting the shaft portion of a locator as defined above through said orifice into said cavity in a predetermined position and providing said veterinary services using said locator.

Preferably the retaining means of said locator is attached to the exterior of said animal.

In one alternative said veterinary service is the detection of a condition in said animal.

Alternatively said veterinary service is the delivery of a fluid to said cavity.

Alternatively said veterinary service is the delivery of seminal fluid and said body cavity is a vagina.

Alternatively said veterinary service is the extraction of a fluid from said body cavity.

BRIEF DESCRIPTION OF THE DRAWINGS

The invention may be more fully understood by having reference to the accompanying drawings wherein.

DETAILED DESCRIPTION OF THE DRAWINGS

Body Mounted Apparatus

Although the preferred embodiment of the apparatus described herein below is such an apparatus installed on a cow with a locator in the vagina of the cow, it will be appreciated that the principles of the invention may be applied to other animals and to other cavities, eg the buccal or nasal cavities. In the case of buccal and nasal applications, a halter may be used to secure the locator to the animal.

Like features are numbered alike throughout the description of the drawings.

Figure 1:
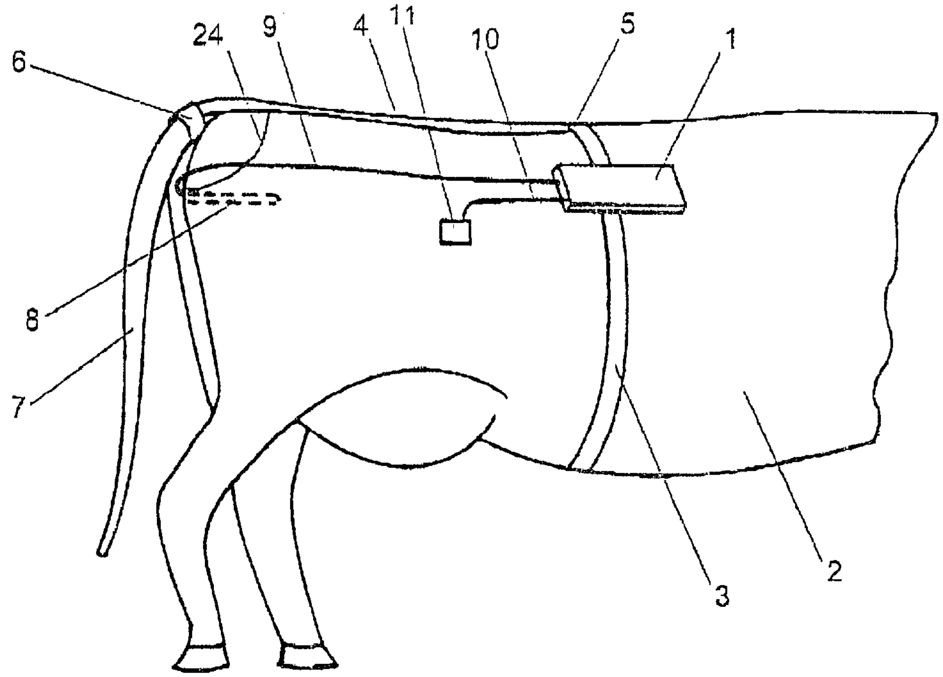
FIG. 1 is a side elevational view of one embodiment of the apparatus of the invention secured with a first embodiment of a harness to a cow with the locator inserted into the vagina of the cow.

In FIG. 1 device 1 contains a reservoir for each therapeutic substance to be delivered to a predetermined site in or on the animal, such as the vaginal cavity or the skin surface of a cow 2. Substances to be delivered to the vagina of a cow are typically ovulation controlling hormones, such as steroids or prostaglandins. For example, progesterone dissolved in a mixture of vegetable oil and benzyl alcohol or in dimethyl sulphoxide can be used.

The device 1 is secured to the outside of the cow by attachment to a strap 3 of a harness. A second strap 4 lies along the back of the animal and is retained by a strap (not shown) under its tail, or by a tubular loop 6 around its tail 7. Straps 3 and 4 are joined at interconnection 5.

A second embodiment of the harness forming a part of the apparatus for remaining it on the back of a cow is illustrated with reference to FIGS. 1A and 2A. The harness consists of a front section 42 and a rear section 44. The sections are constructed to take into account the anatomy of the animal on which they are fined. In the case of a cow 2 the front portion 42 can be made of Dexible material having some degree of stiffness. Polypropylene or nylon or other similar material might be used for this purpose. The degree of stiffness allows it to remain in position on the back of the animal. A shaped piece of relatively stiff plastic may be inserted between stitched layers of, or in a pocket formed in, the flexible material of the front portion 42 for his purpose. Attached to either side of the front portion 42 is an elasticised strap 46 which terminates in strap portions 48. The strap portions are secured together beneath the beast by means of a fastener 50 such as a hook and loop fastener. Strap portions 49 extend rearwardly and forwardly from front section 42 and rear section 44 respectively. They are adjustably joined at connector 52.

The rear section 44 includes darts 62 which provide the rear section with a concave or bowl shape which conforms to the shape of the rump of the animal. A pouch 54 with a dividing strap 56 running along the spine of the animal are provided to secure a device 1. Device 1 may be divided to fit into the hollows to either side of the spine of the animal.

At the rear end of rear section 44 is a tail tube 58 which wraps around the tail 7 of a beast and is secured by a loop portion 61 and a hook portion 60 of a loop and hook fastener. A pair of line end holders located at darts 62 are provided at the rear of rear section 44 to secure a line 24 as illustrated in FIGS. 1 and 2 when holding a locator within the vagina of a cow.

Figure 2:
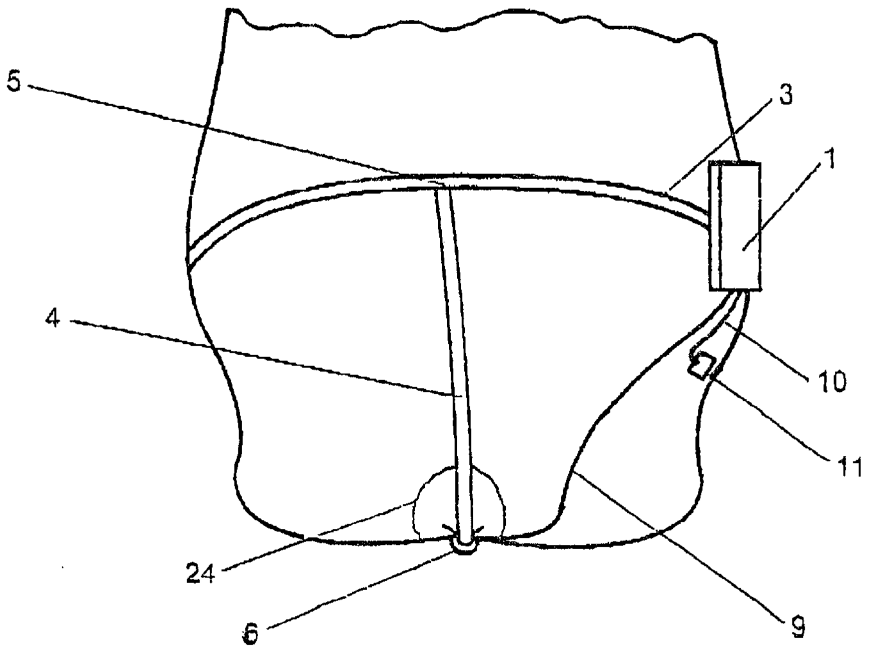
FIG. 2 is a top plan view of the embodiment of FIG. 1.
Figure 1A:
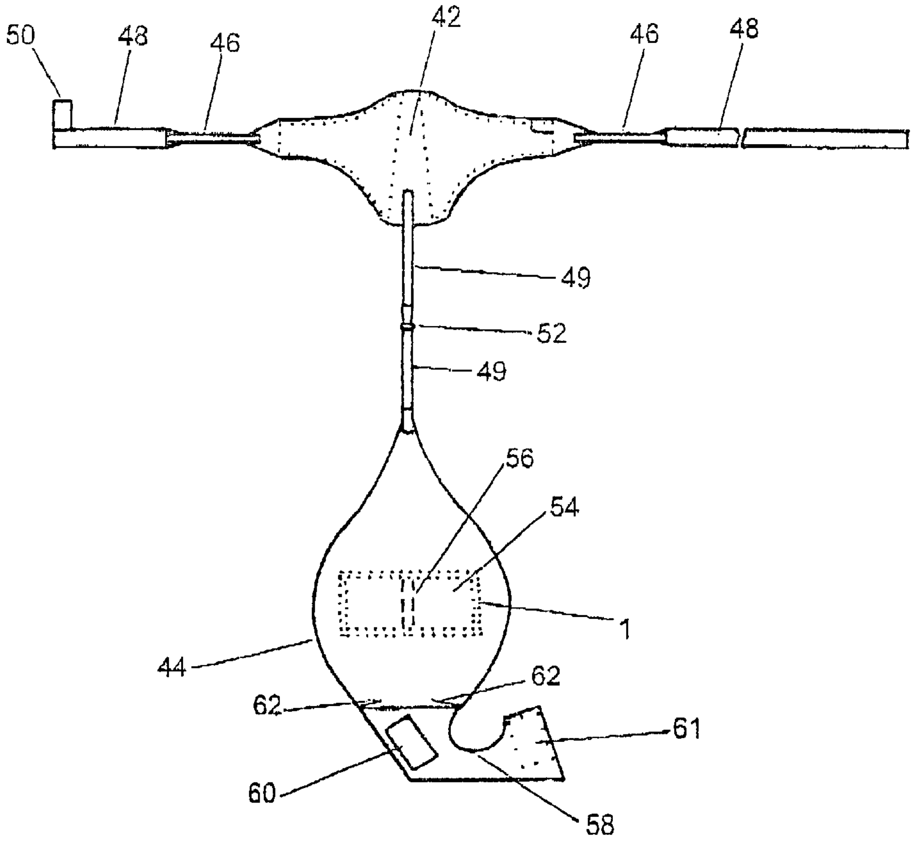
FIG. 1A is a top plan view embodiment of a harness for securing the apparatus according to invention an animal.
Figure 2A:
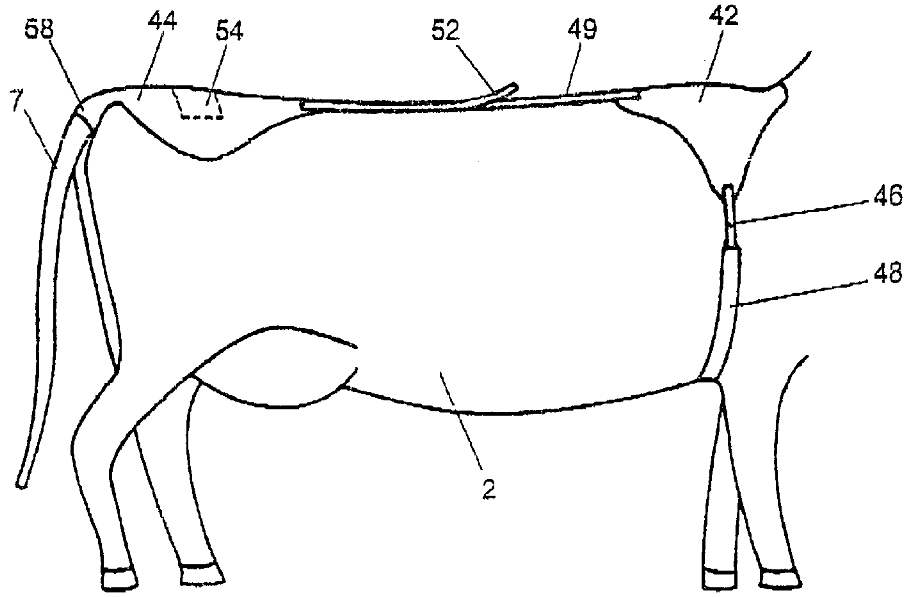
FIG. 2A is a side elevational view of a cow on which the second embodiment of the harness for attaching the apparatus to the animal has been fitted.

The apparatus illustrated in FIGS. 1A and 2A is operated in a similar manner as that in FIGS. 1 and 2. The forward strap encircling the girth of the animal in the embodiment illustrated in FIGS. 1A and 2A is located in a more forward position than that of the embodiment illustrated in FIGS. 1 and 2. One advantage of the arrangement of this embodiment of a harness is that it is less likely to be dislodged by the actions of the beast wearing it or by the actions of other beasts attracted by it. Other advantages are the re-location of the apparatus 1 and girthncircling strap, away from the widest point of the animal where they may be easily snagged.

While any number of substances can be delivered to the cow simultaneously or sequentially by the device 1, the following description will relate to the example of a device for delivering three therapeutic substances.

Figure 3:
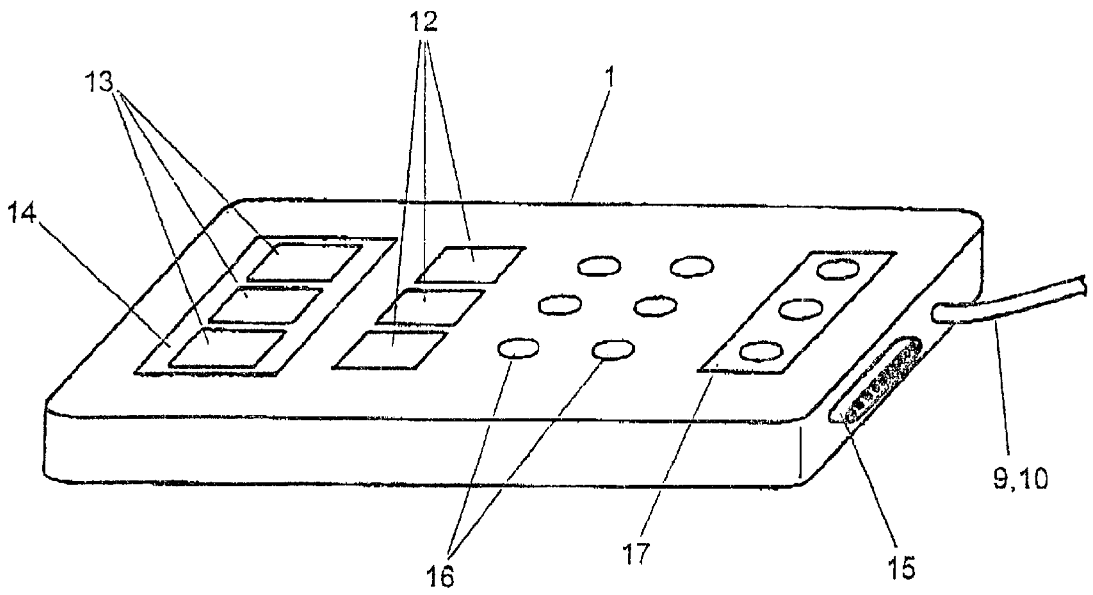
FIG. 3 is a perspective view of one embodiment according to the invention of a housing containing reservoirs, pumps and the controlling microprocessor.

For each of the three substances to be delivered, the device 1, as best seen in FIG. 3, contains a pump 12, a first port of which is connected via a conduit to a chamber or reservoir 13 of a cartridge 14. Each pump 12 has a second port which is connected to the proximal end of a conduit 9 or 10. The conduits 9, 10 have at least one bore or contain at least one tube. The conduits 9, 10 enable transport of substances to distal ends of the conduits located at predeterminedsitcs in or on the animal. The distal ends of the conduits 9, 10 are maintained at the predetermined sites by locators.

The term 'locator' is intended to refer to a device used to maintain at least one end of a conduit at a selected or predetermined location or site in or on the body of an animal. The locator maintains the conduit end at the selected or predetermined location during use of the substance transport device. In some applications the locator may be used to initially introduce the conduit end via a natural orifice, to locate the conduit end at the selected or predetermined location within a natural cavity in the body of the animal, and to then maintain the conduit end at that location during use of the substance transport device. FIGS. 5 to 12 show various embodiments of a locator 8 for maintaining the distal end of the conduit 9 at a predetermined location within the vaginal cavity of a cow. The locator also facilitates the initial insertion of the distal end of the conduit into the vaginal cavity by manipulation. The locator 8 is made with sufficient rigidity so that it can be fully inserted into the vaginal cavity without substantial deformation. The construction and operation of locater 8 is described below.

The distal end of a second conduit 10, seen in FIGS. 1 and 2, terminates at a skin patch 11 that is adhered to the skin of the cow by an adhesive. Alternadvely, a skin patch may be secured by one of the straps 3, 4 of the harness. The skin patch 11 provides for transdermal delivery of substances through the skin or hide of the animal.

The device 1, as best seen in FIG. 3, preferably con and a controller, such as a microprocessor, which is programmed to control the action of a pump driver and thereby the pumps 12 in order that the timing of the delivery of the three substances can be controlled. A veterinarian or a farmer can control the fertility of a cow by controlling the delivery of one or more substances that influence the fertility of the cow. In addition, the fertility of two or more cows can be synlchronised by controlling the time at which a particular hormone, such as progesterone, is delivered to each cow.

The cartridge 14 contains three chambers or reservoirs 13. Each chamber or reservoir 13 preferably contains a single substance to be delivered to the cow. Each chamber or reservoir 13 has an outlet connected to a respective pump 12. The cartridge 14 is detachable so that when it is empty, or is otherwise no longer required, it can be discarded and replaced by a new cartridge if required. The cartridge can include coding which identifies the cartridge and its contents to the pump controller. Preferably the cartridge includes a data storage device which is loaded with data identifying the contents of the cartridge. The stored data is read and loaded into the controller. The controller then provides a pump control routine appropriate to the contents of the cartridge without requiring any intervention from an operator other than the loading of a cartridge into the delivery device.

Data derived from monitoring the operation of the device or data derived from sensors monitoring animal parameters may be loaded into the data storage device of the cartridge and downloaded upon return of the cartridge to a supplier, after use and removal from the delivery device. Such data could include the number, duration and timing of pumping cycles, the battery charge level, various animal body temperatures, and the number and timing of mountings of the animal by other animals. To facilitate gathering data on mountings a pressure sensor may be attached to the strap 4 and connected to the controller of the delivery device.

The microprocessor for controlling the delivery of the three substances is attached to an electronic circuit board which may be linked to an external connector 15. The connector 15 is used to temporarily connect the microprocessor to a computer or other programming device enabling the microprocessor to be programmed for specific delivery requirements for the cow. In the field, connection 15 will be scaled by a water tight cover.

The device 1 may have several indicator lights 16 and may additionally have a liquid crystal display 17. The indicator lights 16 can be used to show whether the cow is currently receiving a substance, when fertility of the cow is optimal for insemination, or other body states of the cow, The indicator lights can also provide an indication of the operation of the device 1. The liquid crystal display 17 can display such features as the programme type, dates for delivery, the elapsed time of treatment, and information as to problems or disorders.

The device 1 may additionally have an alphanumeric key pad, not shown, for programming the operation of the device 1. Altematively, the device 1 can be adapted to be received by a cradle similar to a cradle used for a cordless telephone. The device 1 can be placed in the cradle and data downloaded into the memory of the microprocessor. Further, the cradle can be used to read information from the microprocessor that might not otherwise be displayable on the liquid crystal display 17 or where the device 1 does not have a liquid crystal display 17.

In a preferred embodiment, each pump 12 is a small peristaltic pump 12 driven by a pump driver powered by a three volt electric motor. Each pump 12 has a pump driver 30 dedicated to it. The motor drives reduction gears to reduce the speed of the pump driver, for example, by a factor of approximately 400 to approximately 1 revolution per second without load. The use of reduction gears to reduce the speed of the pump driver increases the leverage thereby providing the pump driver with increase torque. The reduction gears are typically made of a moulded plastics material, such as nylon. The pumps may be driven in either direction so that a substance stored in a reservoir can be delivered to a predetermined site or a substance can be collected from a predetermined site and stored in a reservoir.

The device 1 can deliver one or more substances to one or more sites in or on the animal body and/or collect one or more substances from one or more sites in or on the animal body.

The device 1 can also operate as an indicating means to indicate conditions of the cow or its environment. To this end a sensor can be incorporated with the device, for example integrated with the locator means 8 and inserted into the cow's vagina. The conduit 9 could therefore contain a wire, or the like, for transmitting a signal from the sensor to the device 1. One or more sensors can be used to sense one or more body conditions (for example, a thermocouple thernistor or semiconductor device may sense temperature) or sensors can be used to monitor one or more parameters of the ambient environment in the vicinity of the animal. Sensors may be located at one or more sites in or on the body of the animal. Sensors may be sited at a substance delivery or collecting site.

Following processing of the information gathered from the sensing means by the microprocessor an indication means, for example indicating lights 16 or liquid crystal display 17, can be activated to display the desired information. For example, a pressure sensitive sensor may monitor the mounting, of the animal by another. The time at which, and/or the number of times that, the animal is mounted by another may be stored in a memory or data store in the controller This information, optionally in conjunction with data from a temperature sensor monitoring the body temperature of the animal, may be used to activate an indication means, e.g. lights 16 or display 17. Such an indication may help a veterinarian or a farmer determine a physical condition of the animal, such as its probable fertility state.

A determination, eg of a condition of the animal, may be made by the microprocessor or controller and may be responsive to information aggregated from a plurality of sensors and/or from a series of readings from a single sensor. The substance delivery and/or collection may be responsive to a determination of one or more sensed conditions monitored by the device.

The device includes a holder for accommodating an energy source such as a storage battery that can be either replaced or recharged when necessary. The device may include one or more solar cells for recharging an energy storage device from ambient solar radiation.

Where the locator is maintaining the end of a conduit at site within a body cavity of the animal, the locator can engage the interior surfaces of the cavity. For example, an intra-vaginal locator may be pre-shaped to conform to the shape of the vaginal cavity to retain the conduit end in place at the predetermined site.

The conduits, pumps and reservoirs are preferably provided with protection so that the substances contained therein are protected from adverse effects of solar radiation such as a deterioration caused by excessive temperature rise. Such protection may be provided by reflective layers or coating. A reflective material, e.g. titanium dioxide, may be loaded or incorporated into the material of the walls of the conduits or tubes transporting the substances about the animal. Alternatively, the tubes or conduits may be provided with a reflective layer. Such protection may not be necessary where the animals are to be raised in conditions where there is not a concern about ultraviolet or other solar radiation.

Figure 4:
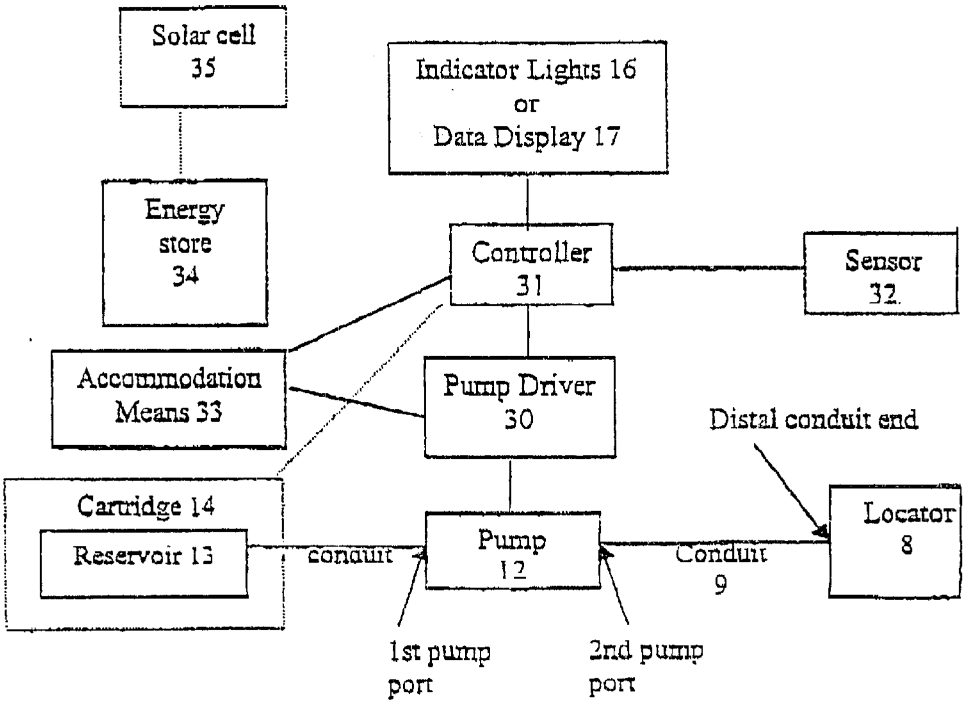
FIG. 4 is a block diagram of an alternative arrangement of the components of the housing of FIG. 3.

FIG. 4 is a block diagram showing a second embodiment for transporting a substance between a single reservoir 13 and a single predetermined site in or on an animal. Equivalent components of the three-reservoir version discussed above are denoted by like numerals A reservoir 13 in a removable cartridge 14 is connected via a conduit to a first port of a pump 12 The distal end of a conduit 9 connected to the second port of the pump is retained at the predetermined site by a locator 8. The pump is driven by a pump driver 30 under control of a controller 31. The controller and pump driver are energised from an energy store 34, such as a rechargeable battery, carried in a battery holder or energy store accommodation means 33. The rechargeable energy store may be recharged from an optional solar cell 35. A sensor 32, monitoring operation of the substance transport device or parameters of the animal or its environment, is connected to the controller. Data gathered is displayed directly, or analysed before display, on indicator lights 16 or data display 17. Data may be stored for later retrieval and analysis.

The controller 31 may receive information from identifying coding data on the cartridge 14. This coding data may be carried in a data store included in the cartridge. Data on the operation of the substance transport device or data gathered from sensors may be downloaded from the controller into the data store in the cartridge for subsequent retrieval after the cartridge has been removed from the device.

The controller may revert to a 'sleep' or low power consumption mode between times at which the pump is activated, to conserve energy and prolong the life of batteries or other source of energy used.

Figure 8:
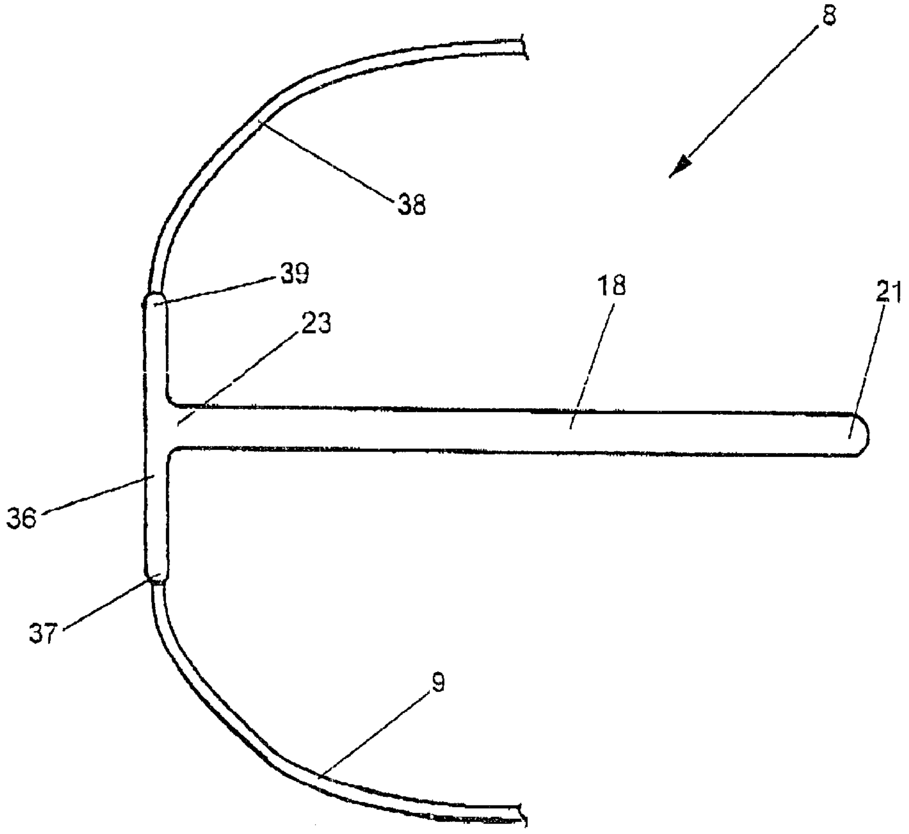
FIG. 8 is a top plan view of a fourth embodiment of a locator.

FIG. 8 shows a first embodiment for applications in which it is desired to locate one end of a conduit at a predetermined location within the vaginal cavity of a cow, A locator 8 is formed integrally with a flexible tubular conduit 9 by a tickening of an end portion of the tubular conduit. The end portion of the conduit forms a main elongate shaft 18 of the introducer. The main shaft 18 is stiffened sufficiently to allow it to be inserted into the vagina without substantial deformation but is flexible enough to conform to the general shape of the vaginal canal.

The conduit 9 is tubular and allows transport a fluid substance. The conduit 9 extends through the main shaft 18 to a port or ports 20 at, or in the vicinity of a first distal end 21. The ports 20 may be openings or may be permeable areas. The distal end 21 of the main shaft may be bulbous. A ring 22 is fitted at the second proximal end 23 of the main shaft. A line 24, e.g. a cord or strap, is fitted through the ring.

The main shaft 18 of the locator 8 is inserted, distal end 21 first, into the vaginal cavity by manipulation. The main shaft is fully inserted so that its proximal end 23 lies at the entrance to the vagina. Part of the line 24 lies transversely to the main shaft 18 and lies across the vaginal entrance to maintain the proximal end 23 of the main shaft at the entrance to the vagina. The line 24 is secured, without slackness, to the exterior of the animal. The line prevents expulsion of the main shaft 18 from the vagina and prevents further penetration of the main shaft 18 into the vagina. The line maintains the outer proximal end 23 of the main shaft substantially at the entrance to the vagina. This control of the depth of penetration, in conjunction with the choice of the length of the main shaft, ensures that the conduit port or ports 20 are retained at a predetermined distance into the vagina. In one arrangement, the length of the main shaft 18 is substantially equal to but less than the length of the vaginal canal, so that the port or ports lie in the vicinity of the cervix. The tie line or cord 24 is preferably elasticated. The two ends (not shown) of the cord are connected to a harness or fixed to the skin or hide directly or to a pad which is secured to skin or hide. The cord 24 passes down one side of the tail across the entrance to the vagina, and up the other side to form a loop. To be expelled, the whole introducer must come out of the vagina. The elasticated cords, when secured to the exterior of the animal, prevent this from happening.

Figure 5:
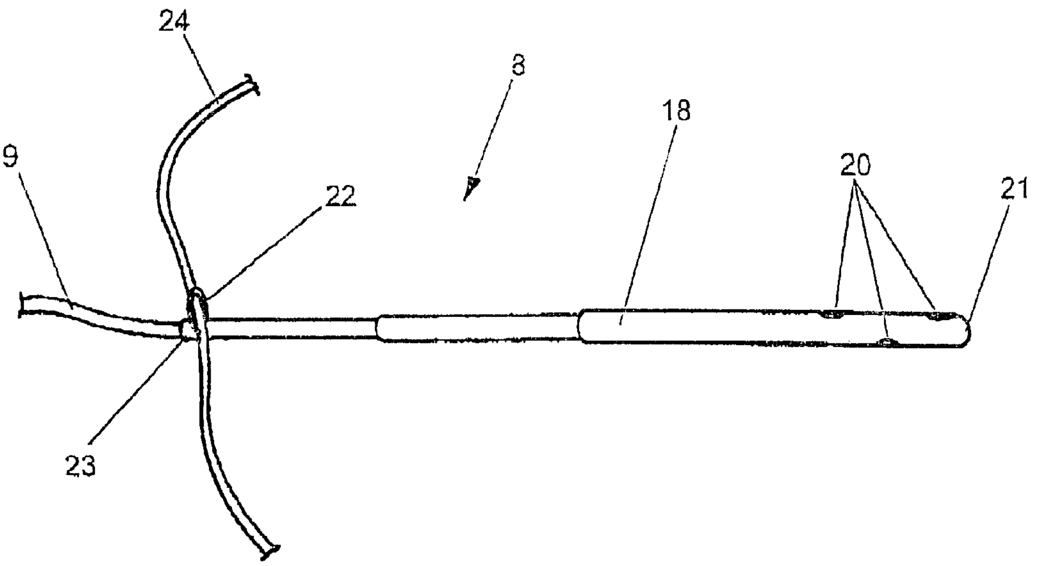
FIG. 5 is a side elevation of a first embodiment of a locator according to the invention.
Figure 6:
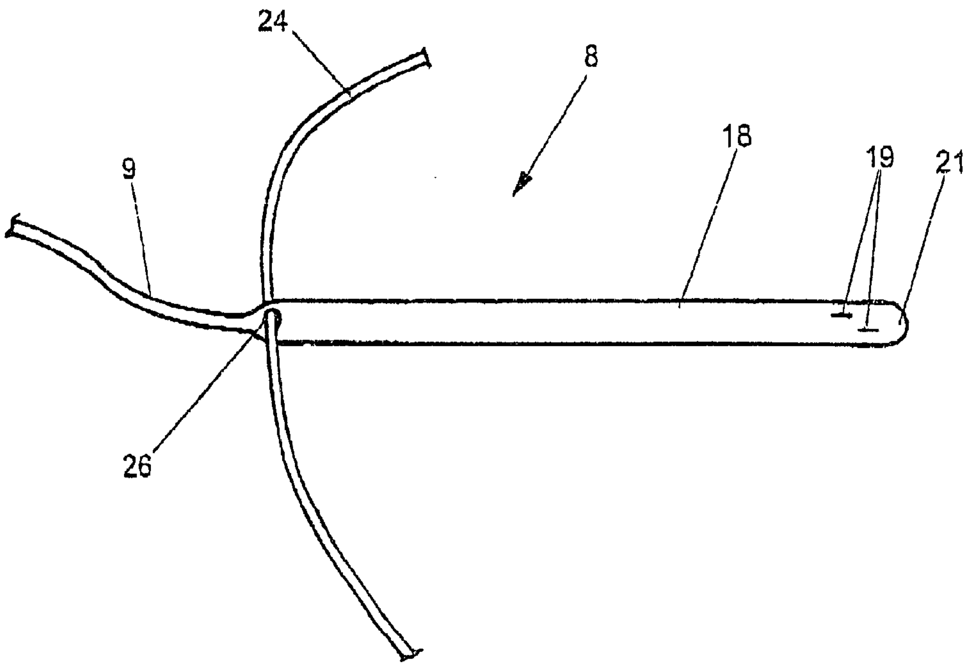
FIG. 6 is a side elevation of a second embodiment of a locator.

FIG. 6 shows an alternative to the arrangement of FIG. 5 where the ring 23 shown in FIG. 5 is replaced by an aperture 26 integrally formed in the proximal end 23 of the main shaft 18 of the locator 8.

Figure 7:
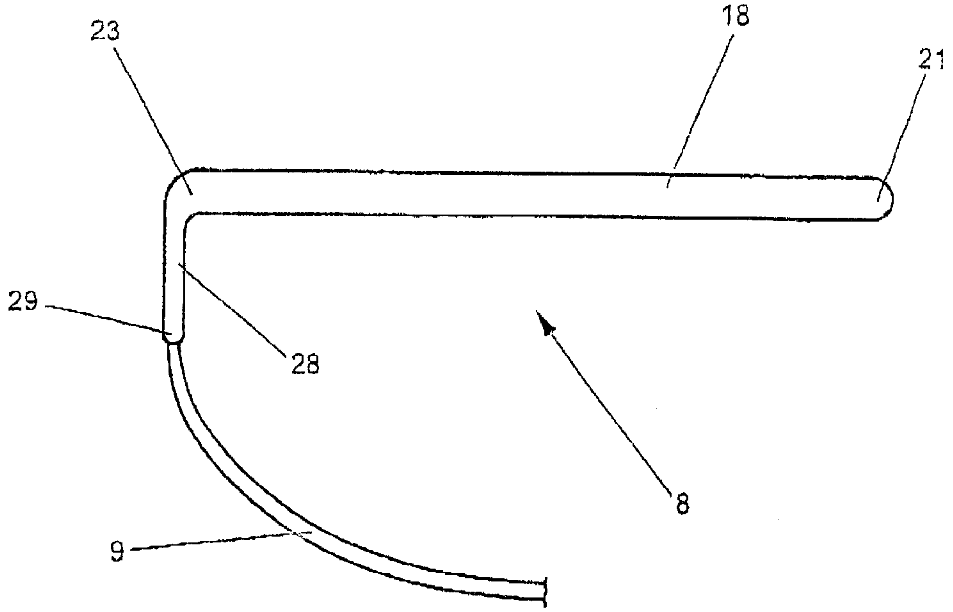
FIG. 7 is a top plan view of a third embodiment of a locator.
Figure 9:
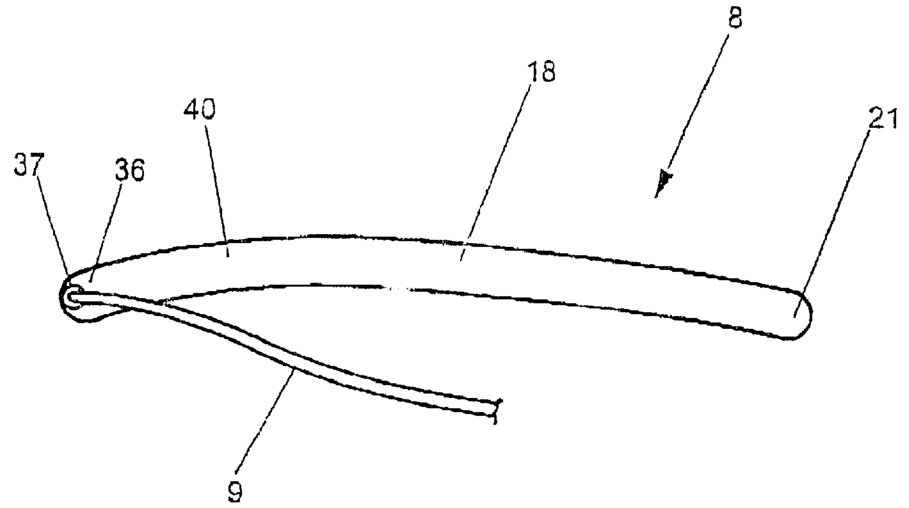
FIG. 9 is a side elevational view of a fifth embodiment of a locator.

FIGS. 7, 8 and 9 show locators in which control of the depth of penetration of the introducer is provided by a formation extending transversely to the main shaft at the second end thereof Preferably, the transverse formation is integrally formed with the main shaft. Preferably, the transverse formation does not extend rigidly behind the outer end of the main shaft.

FIG. 7 shows an L-shaped locator 8 in which an extension 28 extends in a single direction from the proximal end 23 of the main shaft 18 of the locator 8 The conduit 9 may be attached to the main shaft 18 and extension 28 but is preferably integrally formed to extend from the distal end 21 of the main shaft 18 to the distal end 29 of the extension 28. The conduit 9 may be used to secure the introducer 8 to the animal. Alternatively, a strap or tie line fixed to the distal end 29 of the transverse extension 28 may be used to secure the introducer to the animal.

FIG. 8 shows an T-shaped introducer in which an extension 36 extends in two opposite directions from the proximal end 23 of the main shaft 18 of th locator 8. The conduit 9 may be attached to the main shaft and extension but is preferably integrally formed to extend from the distal end 21 of the main shaft 18 to one distal end 37 of the extension 36. The conduit 9 may be used to secure the locator 8 to the animal. A tie line 38 is attached to a second distal end 39 of the extension 36. The tie line 38 is used to secure the locator 8 to the animal. In one arrangement, a respective the line is attached to each of the two distal ends 37, 39 of the extension 36 and secured to a respective side of the animal, e.g. to a pad fixed to the skin or hide of the animal, or to points on a harness worn by the animal.

Figure 10:
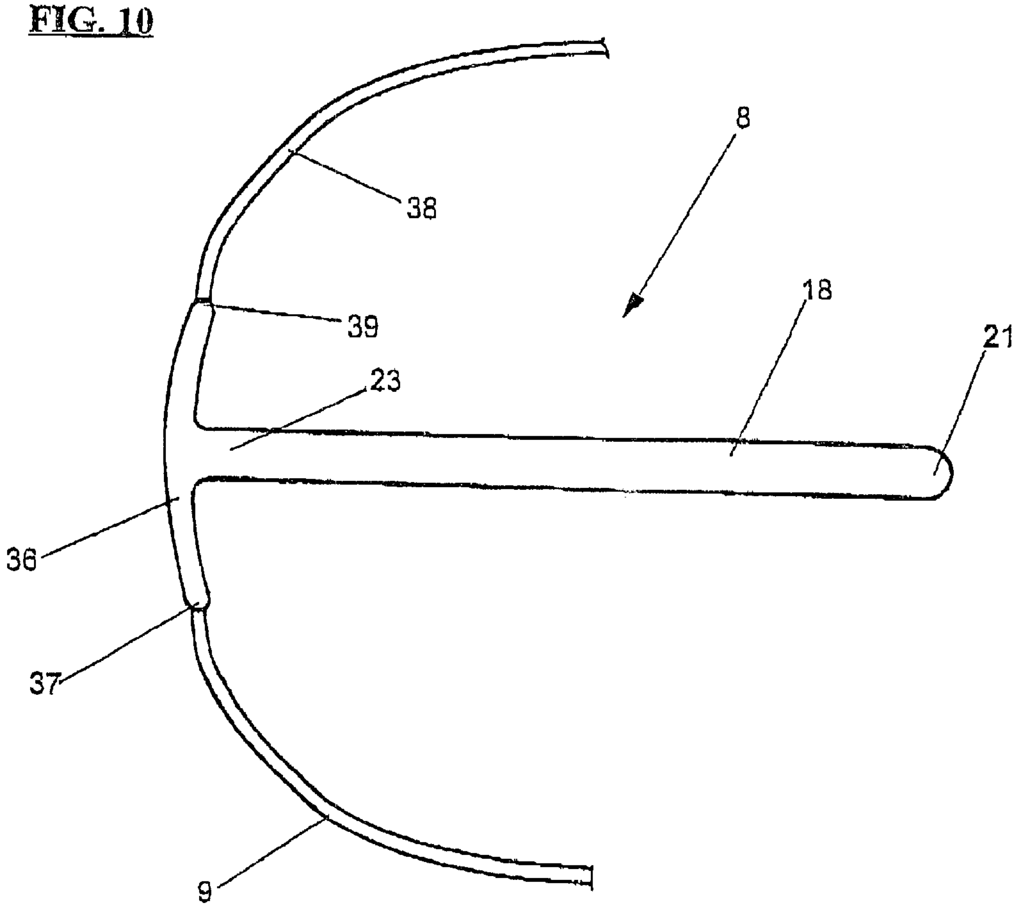
FIG. 10 is a top plan view of a sixth embodiment of a locator.
Figure 11:
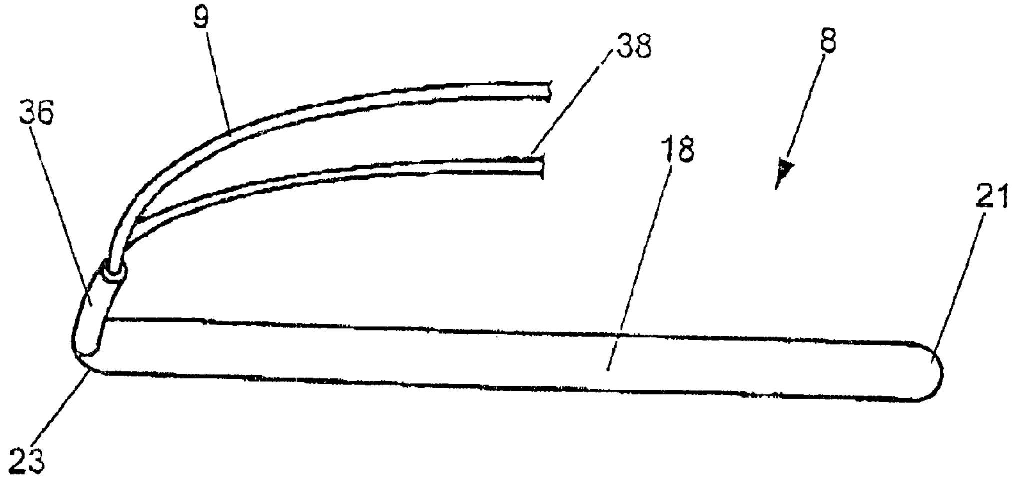
FIG. 11 is a side elevation of the embodiment of the locator illustrated in FIG. 10.
Figure 12:
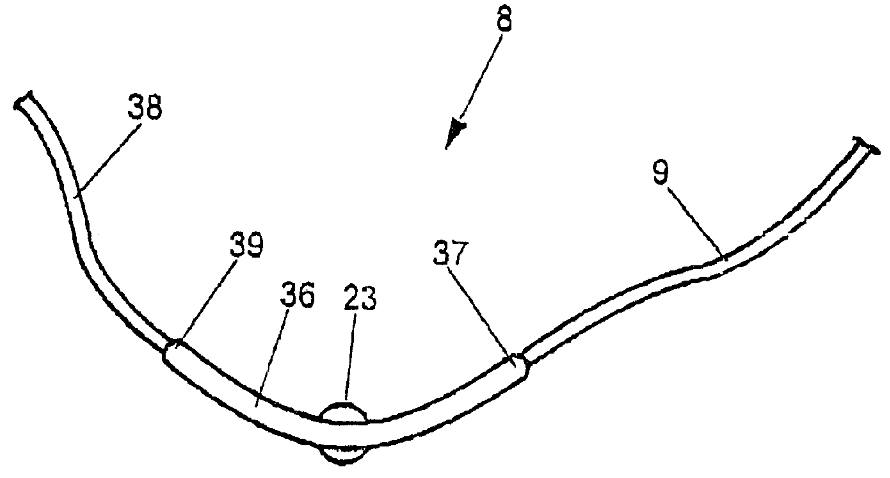
FIG. 12 is an end elevation of the embodiment of the locator illustrated in FIGS. 10 and 11.

FIGS. 10, 11 and 12 show a modification of the T-shaped arrangement shown in FIG. 8. The extension 36 is curved to present a convex shape at the proximate end 23 of the main shaft 18. The curved extension is engaged by the animal's tail as it sweeps from side to side. This engagement helps to retain the introducer in position by pushing the main shaft into the vagina. The convex curve also helps, in conjunction with the lack of any rigid extension behind the second end of the main shaft, to reduce chafing at the underside of the base of the tail.

The transverse extensions of the 'T' or 'L' shaped locators limit the degree of penetration of the introducer into the vagina and ensure that the port in the conduit is held at a predetermined distance from the entrance to the vagina.

The distal ends of the transverse part at the end of the 'T' or 'L' shape may be tied or otherwise attached to elasticated cords. The distal ends of the transverse parts may include an aperture through which the tie cord can be fitted. Part of the length of the conduit may be used as part of the length of a tie cord. The tie cords may be connected to a pad or pads attached, such as by adhesive, to the skin or hide of the animal. Alternatively, the cords may be attached to a harness fitted to the animal. The cords retain the locator in the vagina and, in conjunction with the transverse parts of the 'T' or 'L' shape, keep the locator in the correct orientation. To be expelled, the whole of locator must come out of the vagina but the cords, when attached to the exterior of the animal, prevent this from happening.

When the distal ends of the transverse 'T' piece are attached to the exterior of the animal, the position of the locator is responsive to actions of the animal. For example, while the animal is standing normally the locator is under no strain but when the animal arches its back to void, added tension applied through the tie cords pulls the outer end of the main shaft of the locator up and into the vagina. The upward pressure pulls the introducer away from the urethral opening at the base of the vulva. The strain pulling the locator into the vagina pulls it away from the voiding faeces, reducing faecal build-up common with other intra-vaginal devices.

In the embodiments of the locator described above, the main shaft of the locator is shown as being straight. Alternatively, the main shaft of the locator may be substantially pre-shaped to conform to the internal anatomy of the vagina. FIG. 9 shows a locator 8 in which the main shaft 18 is curved. The main shaft 18 lies generally in one plane, the plane being perpendicular to the transverse extension 36, and is pre-shaped with a curve 40 to conform to the pelvic rise in the vaginal canal. The conduit 9 is formed to be integral with the main shaft 18 and distal end 37 of extension 36. Tie line 38 is not visible in FIG. 9.

The curvature of the main shaft can be used to control the orientation and the depth of penetration of the main shaft in the vaginal cavity. The retention of the locator at a particular position in the vaginal cavity can be maintained by the curvature in the main shaft either with or without any other means of retention or penetration control.

In another embodiment, the locator 8 includes a conduit 9 comprising at least two tubes. One of the tubes is used for the transport of fluid substances. A rigid rod or wire is inserted in the bore of another of the tubes, the rod or wire being bent to pre-shape the main shaft of the locator.

In a preferred arrangement for the delivery of fluid substances to a predetermined site the vaginal cavity of a cow, one end of a conduit tube is supported at the predetermined site by a locator. The end of the conduit tube is sealed and a small slit or slits are made in the wall of the conduit close to the sealed end. The slits are aligned with the axis of the conduit. The other end of the conduit is connected to a pumping system and reservoir. When the pump increases the pressure of fluid in the conduit, the slits open and the fluid is forced out. When the pressure falls the shaft wall is restored to its resting position and the slits close. This simple one-way valve eliminates or at least reduces problems associated with mucous blockage.

In another application illustrated in FIG. 6, one end of tubular conduit 9 is integrated into the locator 8. The other end of the conduit 9 connects to a pumping system and reservoir. The conduit terminates at slit or slits 19 made in the wall of the shaft 18. The slit or slits are aligned with the axis of the shaft. The slit or slits open to discharge fluid when the fluid pressure in the conduit in the shaft increases under action of the pump. When the fluid pressure falls the shaft wall is restored to its resting position and the slit or slits close.

In another alternative arrangement fluid is delivered from a reservoir to a predetermined site in a natural body cavity via a conduit without the use of a pump. The reservoir is secured w the animal at a position that is above the predate ed site and fluid is delivered under the force of gravity. In one example of a gravity fed arrangement, a reservoir is attached to the body of an animal and a conduit connects the reservoir to a delivery site in the buccal cavity. Fluid is delivered to the cavity when the animal lowers its head to feed. Fluid delivery ceases when the animal raises its head and thereby reduces the "head" or elevation of the reservoir above the delivery site.

In yet another arrangement, the reservoir is integrated into the locator and fluid is transported between the reservoir and a port in the locator. This arrangement allows for a fluid management device that may be retained totally within a body cavity. Such a device if fitted totally within a body cavity, may retain the port at a predetermined site without the need for an external securing arrangement by the use of a locator shaped to conform to the shape of the cavity, eg. a curvature to conform to the pelvic rise of a vaginal cavity.

In another embodiment such a locator may be positioned so that fluid within a body cavity flows by gravity into a reservoir within the locator.

The locator may also be used to position the end of a conduit for transporting signals at a predetermined location within a natural body cavity. The conduit may include a wire or wires connected to a sensor or transducer located in the main shaft of the locator. The conduit may carry signals from a sensor monitoring the environment in the vicinity of the cavity to a data management device mounted externally on the animal.

It is to be noted that other locator arrangements may include the features disclosed above in different combinations than those described above, For example, the open or permeable ports described in relation to the embodiment of FIG. 5, or the slit valves described in relation to the embodiment of FIG. 6, may be present in any of the other configurations described. Similarly, the curving of the main shaft shown in the embodiment of FIG. 9 may be present in any of the other locator arrangements described.

Locator Without Harness

Intervaginal devices known in the prior art use a variable geometry to prevent the device from falling out of the vagina. Intervaginal devices can be expelled when the animal shortens the length of the vaginal canal. Devices can also be expelled by a peristaltic wave that squeezes the device out. The variable geometry of prior art devices usually consists of laterally arm on the devices which extend after it has been inserted to jam the device within the cavity.

A locator according to the invention intended to be used in the vaginal cavity of animals has no lateral projections. The sectional area of the locator is small providing little substance for a peristaltic wave to gain purchase to expel the device. The locator is shorter than the vaginal canal so that shortening of the canal does not eject the locator.

The description of the various embodiments of the locator in FIGS. 5–12 has been for use in conjunction with the harness illustrated in FIGS. 1, 1*a*, 2 and 2*a*. In another embodiment it is possible to use the locator of FIGS. 5–12 as an Intervaginal device for the delivery of veterinarian services without the remaining components illustrated and discussed with reference to FIGS. 14. The preferred shape for such a purpose is that illustrated in FIG. 9. The shaft 18 of the locator 8 has a bend 40 which coincides with the natural shape of the vagina of a cow. The shafts of the other embodiments of locators 8 in FIGS. 5–8 and 10–12 may also have a curve corresponding to curve 40. In the embodiments illustrated locator 8 is attached to retaining lines corresponding to lines 24 and 38, as illustrated, the free ends of which will be attached to the hide of the animal using adhesive patches such as the adhesive patch 1 illustrated in FIG. 1. In each case where there is illustrated a conduit 9, it is a line 24 or 38 which is substituted.

Because the locator 8 is shaped to conform to the inner geometry of the cavity into which it is inserted it is self locating. Thus, if temporarily dislodged it will relocate itself in its predetermined position. Where a locator is provided without a reservoir it could serve to locate one or more sensors at a predetermined site. Placing different sensors at different locations on the locator enables the user to take readings from different predetermined sites within the cavity. A locator could also be provided with an integral reservoir. The reservoir could then be inserted into the body cavity where fluid could be transported between the reservoir and the predetermined site. Such a system is particularly useful when fluids to be transported are to be kept at body temperature. Such a locator with reservoir can be used to collect fluids from a body cavity.

An integral pump may also be provided in association with the reservoir where as an alternative to gravity feed of the fluid contained in it. Among the veterinary services which can be provided in conjunction with locators of the type described are detecting a condition such as oestrus or a fever in an animal, the delivery of a medical or nutritional fluid into a cavity. The delivery of seminal fluid into the uterus of an animal and the extraction of a fluid from a cavity of an animal are other possible veterinarian services.

Head Mounted Embodiments

Figure 13:
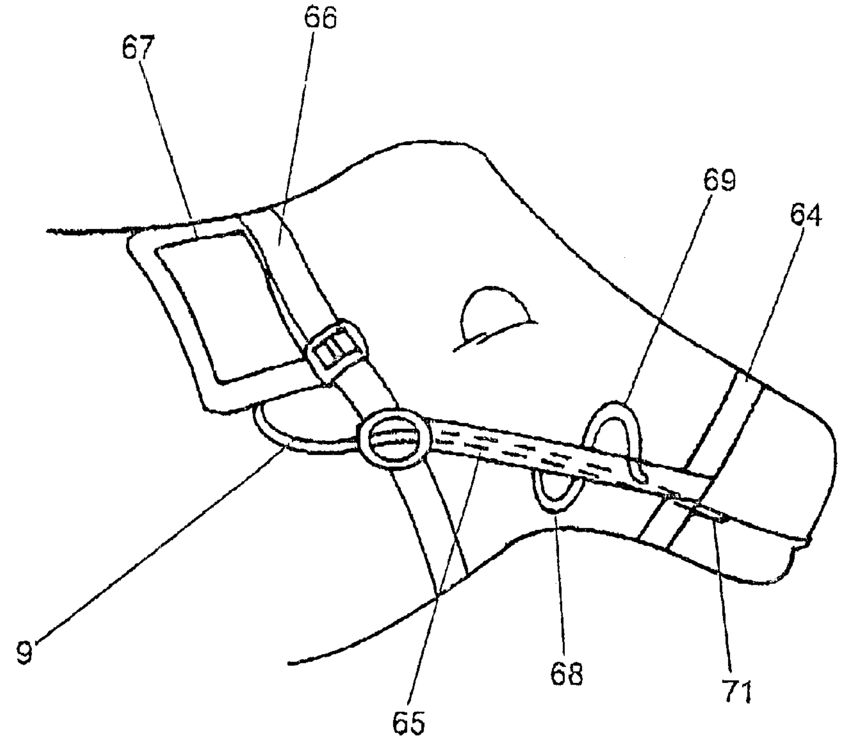
FIG. 13 is a side elevational view of a halter type harness for fitting an embodiment of the invention to the head of the cow.
Figure 14:
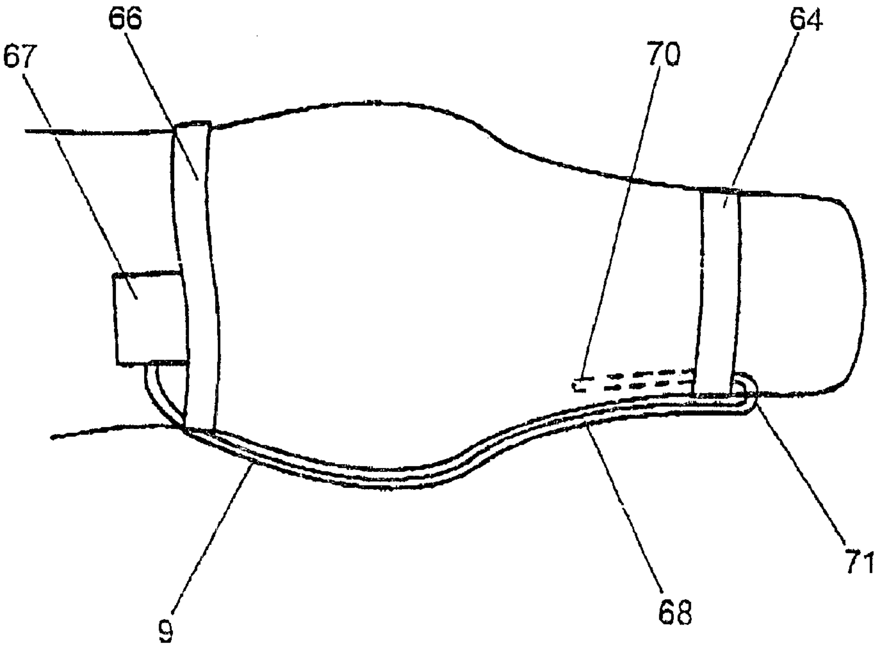
FIG. 14 is a top plan view of the embodiment of FIG. 13 with a locator positioned between the lower teeth and cheek of the animal.
Figure 15:
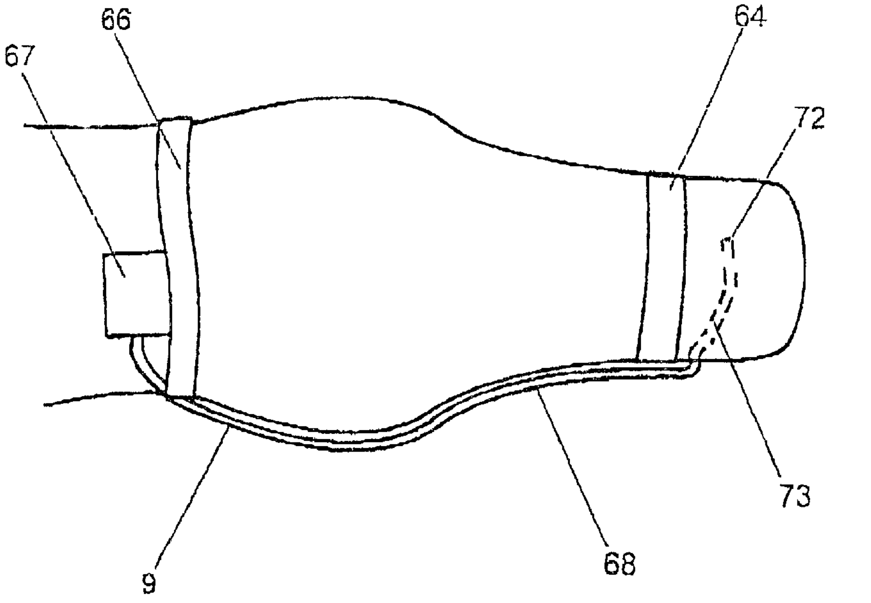
FIG. 15 shows an alternative embodiment to that shown in FIG. 14 with the locator passing through the diastema and discharging a fluid below the tongue.

An embodiment of the invention where the locator is adapted to deliver fluid to the mouth of an animal is illustrated in FIGS. 13 to 15.

In the embodiment illustrated in FIGS. 13 to 15 the beast is fitted with a halter consisting of a nose band 64, a neck band 66 and a pair of cheek straps 65. A reservoir 67 is mounted on neck band 66. A tube 9 flows out of reservoir 67 along cheek strap 65 to a locator 68. The locator 68 is provided with an S-bend 69 in a position where it is outside the mouth of the beast to locate it in an appropriate location.

In the embodiment illustrated in FIG. 14 the locator 68 has a bend 71 through approximately 180°. When installed in position a portion of the locator 68 lies partly within the mouth of the beast between the check and the lower molars. This portion has an outlet 70 in the mouth of the beast slightly rearward of the molars.

In the alterative embodiment illustrated in FIG. 15 the locator 68 bends at 73 in the direction illustrated to pass through the diastema between the lower incisors and molars of a ruminant, The outlet 72 of the locator 68 for the embodiment illustrated is beneath the tongue.

It will be appreciated by those skilled in the art that other embodiments of locators may be provided to deliver fluids within the mouths of beasts fitted to the particular beast. The precise dividing line between a conduit 9 and a locator 68 will vary with the type of animal.

In the embodiment illustrated in FIGS. 13 to 15 the apparatus does not need to include a pump. Fluid may be advanced from reservoir 67 to the discharge ends 70 or 72 by gravity when reservoir 67 is at a level higher than the mouth of the beast. The location of the reservoir at the upper region of the neck, above the point of fluid discharge, provides for fluid delivery by gravity feed when the position of the head of the animal is at at least some of the positions normally encountered. A flow restricted may be employed to ensure delivery occurs at the correct time. It is possible to provide a microprocessor and a detector to actuate a solenoid valve to supply fluid from the reservoir at a time which is required.

Figure 16:
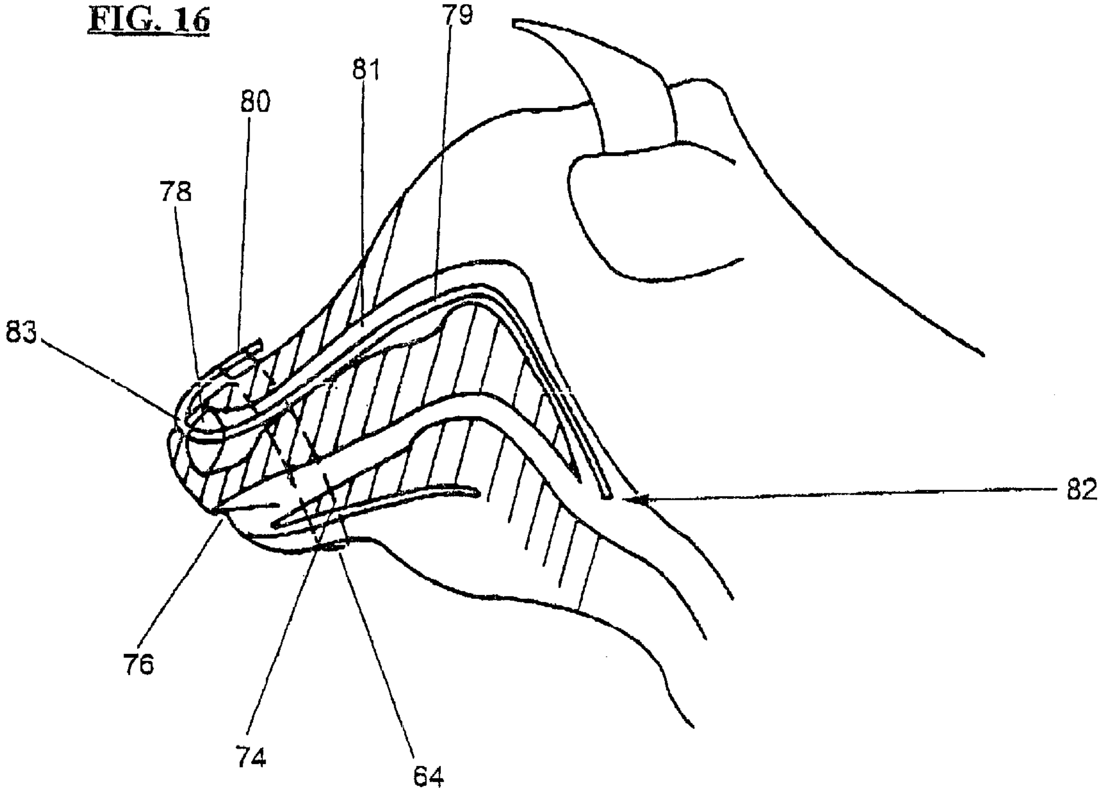
FIG. 16 is a side view partially cut away of a locator installed in the nasal passage of an animal

An alternative embodiment of locator is illustrated with reference to FIG. 16. This is intended to deliver a fluid through a nasal passage. The cut away portion of the animal's head illustrates the tongue 74, the mouth 76 and the entrance 78 leading to nasal passage 81.

Locator 79 is of a relatively stiff but flexible material. At its proximal end it is attached at 80 to nose band 64 of a halter as ilutaein FIGS. 13 to 15. In the embodiment illustrated the fluid is delivered from locator 79 through an orifice 82 at the entrance to the oesophagus. A nasal delivery embodiment may be used where it is sought to avoid causing excessive salivation.

The attachmnent 80 of the locator 79 to the nose band 64 prevents it from being dislodged if the beast should sneeze.

The U bend 83 of the nasal locator ensures that the locator 79 does not over penetrate the nasal passage 81 of the beast.

Although in the preferred embodiments of the invention the intention is to deliver a fluid from the reservoir to a body cavity in which the locator has been positioned. It will be appreciated by those skilled in the art that the apparatus can be used to remove fluids from body cavities. When the apparatus is one which is provided with a pump, a change from delivery to collection of fluid will occur when the direction of flow of the pump is reversed. When collection of fluid is contemplated the orifice at or near the distal end of the locator is an intake orifice rather than a discharge orifice.

Other embodiments of the invention within the scope of the appended claim will be apparent to those skilled in the art.

What is claimed is:

1. An apparatus for transporting a fluid through a natural orifice of an animal and into a natural body cavity of said animal, said apparatus comprising:

a reservoir for the fluid, a locator, a part of said locator passing through said natural orifice, conforming with the natural body cavity and being retained at a predetermined position within said natural body cavity for release of said fluid at the predetermined position in the natural body cavity, a penetration controlling device controlling an amount of penetration of the part of said locator into said natural body cavity and an amount of a remainder of the locator located exteriorly of the natural body cavity, whereby the part of the locator is allowed to freely move into and out of said natural body cavity while being retained in the natural body cavity during movement of the animal, a conduit communicating between said reservoir and said part of said locator, an automatic delivery system for advancing said fluid through said conduit between said reservoir and said part of said locator located in said natural body cavity, and said reservoir and said automatic delivery system being securable to the exterior of said animal.

2. The apparatus as claimed in claim 1, wherein said reservoir has at least two compartments and said conduit consists of at least two passages, each said passage communicating with one of one of said compartments and another passage.

3. The apparatus as claimed in claim 1, wherein said reservoir comprises at least one replaceable cartridge.

4. The apparatus as claimed in claim 1, wherein said part of said locator includes an orifice and a portion of said conduit is integral with said locator and communicates with said locator orifice.

5. The apparatus as claimed in claim 1, wherein said penetration controlling device is adapted to engage body surfaces of said animal.

6. The apparatus as claimed in claim 1, wherein said penetration controlling device is adapted to restrain over-penetration of said part of said locator beyond said predetermined position in said natural body cavity for controlled delivery of the fluid to said predetermined position in the natural body cavity.

7. The apparatus as claimed in claim 1, wherein said part of said locator is adapted to be retained in said body cavity by an external retaining portion on said locator being integral with said penetration controlling device.

8. The apparatus as claimed in claim 1, wherein said part of said locator which is adapted to pass through a natural orifice of said body cavity and be fitted for retention at a predetermined position within said body cavity is elongate.

9. The apparatus as claimed in claim 1, wherein said locator is made of semi-rigid material.

10. The apparatus as claimed in claim 1, wherein said automatic delivery system is a pump.

11. The apparatus as claimed in claim 10, wherein said pump is provided with a meter.

12. The apparatus as claimed in claim 10, further comprising a microprocessor for controlling said pump.

13. The apparatus as claimed in claim 12, further comprising a detector associated with said microprocessor.

14. The apparatus as claimed in claim 13, wherein said detector is associated with said locator.

15. The apparatus as claimed in claim 13, wherein said microprocessor is programmable to control said pump to transfer a predetermined amount of fluid at a time and in a volume determined by signals from said detector.

16. The apparatus as claimed in claim 13, wherein said reservoir, pump and microprocessor are located in a housing.

17. The apparatus as claimed in claim 1, wherein said automatic delivery system is gravity.

18. The apparatus as claimed in claim 1, wherein said fluid is transferred from said reservoir to a particular site in said body cavity.

19. The apparatus as claimed in claim 1, wherein said fluid is transferred from said body cavity to said reservoir.

20. The apparatus as claimed in claim 1, wherein said reservoir and said delivery system are secured to an exterior surface of said animal where said animal orifice is rearward facing and said animal is a quadruped having a tail with a proximal end and a distal end by a first strap adapted to extend in use transversely around the body of said animal and a second strap adapted to extend in use longitudinally rearwardly therefrom along a back of said animal and encircle said proximal end of the tail.

21. The apparatus as claimed in claim 20, wherein a pouch on said second strap receives said reservoir and said delivery system.

22. The apparatus as claimed in claim 1, wherein a broadened flexible but stiff portion in said first strap is adapted to assist in use in retaining said reservoir and said delivery system on said animal.

23. The apparatus as claimed in claim 1, wherein said part of said locator is adapted to be retained in said body cavity by an external retaining part on said locator, said external retaining part being attached to said second strap.

24. The apparatus as claimed in claim 1, wherein said penetration controlling device is provided with an external retaining means adapted to be secured with an adhesive to the body of said animal.

25. The apparatus as claimed in claim 1, wherein said locator being adapted to be fitted and retained in a mouth of an animal.

26. The apparatus as claimed in claim 1, wherein said natural body cavity of said animal is a nasal passage of said animal, said locator being adapted to be fitted and retained in said nasal passage.

27. A locator comprising an elongate shaft having a portion adapted to be inserted end first through a natural orifice into a natural body cavity of an animal to sit in a predetermined position, said portion being adapted to self locate in said natural body cavity at said predetermined position, said portion being shaped to conform to said natural body cavity without distorting said natural body cavity, and a penetration control device maintaining said portion of said shaft at said predetermined position in said natural body cavity and maintaining a remaining part of said shaft exteriorly of said natural body cavity, whereby the portion of the shaft is allowed to freely move into and out of said natural body cavity while being retained in the natural body cavity during movement of the animal.

28. The locator as claimed in claim 27, wherein said penetration control device is attachable to said animal.

29. The locator as claimed in claim 27, wherein said shaft is adapted to self locate by the penetration control device being located at a proximal end of said shaft, said penetration control device in use engaging an outer surface of said animal at or adjacent said animal orifice.

30. The locator as claimed in claim 29, wherein said penetration control device includes a lateral extension at the proximal end of said shaft.

31. The locator as claimed in claim 30, wherein said lateral extension extends substantially in a single direction transverse to said portion of the shaft.

32. The locator as claimed in claim 31, wherein said lateral extension extends substantially in two mutually opposite directions transverse to said portion of the shaft.

33. The locator as claimed in claim 27, wherein a sensor associated with said locator senses a condition in said animal.

34. The locator as claimed in claim 27, further comprising an integral reservoir and fluid advancing device.

35. The apparatus as claimed in claim 1, wherein said locator comprises an elongate shaft portion adapted to be inserted end first through a natural orifice into a natural cavity of an animal to sit in a predetermined position, said shaft portion being adapted to self locate in said natural cavity at said predetermined position, said shaft portion being shaped to conform to an interior shape of said body cavity without distorting said cavity.

* * * * *